(12) United States Patent
Hill et al.

(10) Patent No.: US 8,591,748 B2
(45) Date of Patent: *Nov. 26, 2013

(54) WATER TREATMENT

(75) Inventors: John Hill, Plymouth, MN (US); Joseph A. King, Wayzata, MN (US)

(73) Assignee: King Technology, Inc., Hopkins, MN (US)

( * ) Notice: Subject to any disclaimer, the term of this patent is extended or adjusted under 35 U.S.C. 154(b) by 639 days.

This patent is subject to a terminal disclaimer.

(21) Appl. No.: 12/800,692

(22) Filed: May 20, 2010

(65) Prior Publication Data

US 2010/0230365 A1  Sep. 16, 2010

Related U.S. Application Data (60) Continuation-in-part of application No. 12/315,285, filed on Dec. 2, 2008, now Pat. No. 7,875,191, which is a continuation of application No. 11/999,654, filed on Dec. 6, 2007, now Pat. No. 7,501,067, which is a division of application No. 10/928,668, filed on Aug. 26, 2004, now Pat. No. 7,347,934, application No. 12/315,285, which is a continuation-in-part of application No. 12/386,109, filed on Apr. 14, 2009, which is a continuation of application No. 12/001,354, filed on Dec. 11, 2007, application No. 12/315,285, which is a continuation-in-part of application No. 11/648,743, filed on Dec. 29, 2006.

(60) Provisional application No. 61/126,105, filed on May 1, 2008, provisional application No. 60/878,016, filed on Dec. 29, 2006, provisional application No. 60/757,198, filed on Jan. 6, 2006.

(51) Int. Cl.
  *C02F 1/76* (2006.01)
  *C02F 1/50* (2006.01)

(52) U.S. Cl.
  USPC ............................. 210/755; 210/764; 210/192

(58) Field of Classification Search
  USPC ................... 210/754, 755, 756, 764, 739, 746
  See application file for complete search history.

(56) References Cited

U.S. PATENT DOCUMENTS

| | | | |
|---|---|---|---|
| 5,888,428 A * | 3/1999 | Howarth et al. | 210/755 |
| 6,086,746 A * | 7/2000 | Nalepa | 205/500 |
| 2006/0043011 A1 * | 3/2006 | King et al. | 210/754 |

OTHER PUBLICATIONS

EPA, "Swimming Pool Water Disinfectants," DIS/TSS-12, Apr. 23, 1979.*

* cited by examiner

*Primary Examiner* — Lucas Stelling
(74) *Attorney, Agent, or Firm* — Jacobson & Johnson LLC (57) ABSTRACT

A system and method for maintaining a body of water in a sanitized condition with use of a halogen and a source of silver ions wherein the halogen is maintained at 50% to 75% less than a recommended halogen level for maintaining the body of water in a sanitized condition by adding a compound containing a hydantoin ring to a recreational body of water containing a halogen and a source of metal ions.

7 Claims, 8 Drawing Sheets

FIG. 8
pH levels at water sampling

| Date | Solution C pH | Solution D pH |
|---|---|---|
| 4/21 | 7.46 | 7.44 |
| 4/28 | 7.43 | 7.41 |
| 5/5 | - | - |
| 5/12 | 7.45 | 7.42 |
| 5/19 | 7.45 | 7.44 |
| 5/26 | 7.42 | 7.44 |
| Average | 7.44 | 7.43 |

FIG. 9
Dissolved silver concentrations

| Date | Solution C Ag(ppb) | Solution D Ag(ppb) | Ratio |
|---|---|---|---|
| Start | Start | Start | Start |
| 4/21 | 4.3 | 2.8 | 2 |
| 4/28 | 17 | 8.7 | 2 |
| 5/5 | 46 | 2.4 | 19 |
| 5/12 | 86 | 2.9 | 30 |
| 5/19 | 140 | 4.0 | 35 |
| 5/26 | 220 | 7.1 | 31 |
| Average | 86 | 4.7 | 18 |

FIG. 10

(STUDY 1: Silver concentration calculated from solubility product product of AgBr.)

| Spa Study | Week | Bromide (ppm) | Bromide (mol/L) | Calculated Silver (mol.L) | Calculated Silver (ppb) | Actual Silver (ppb) |
|---|---|---|---|---|---|---|
| 1 | 1 | 110 | 0.001377 | 3.8862E-10 | 0.04 | BRL |
| | 2 | 120 | 0.001502 | 3.5624E-10 | 0.04 | BRL |
| | 3 | 130 | 0.001627 | 3.2884E-10 | 0.04 | BRL |
| | 4 | 150 | 0.001877 | 2.8499E-10 | 0.03 | BRL |
| | 5 | 140 | 0.001752 | 3.0535E-10 | 0.03 | BRL |
| | 6 | 160 | 0.002002 | 2.6718E-10 | 0.03 | BRL |
| | 7 | 150 | 0.001877 | 2.8499E-10 | 0.03 | BRL |
| DMH added | 8 | 106 | 0.001327 | 4.0329E-10 | 0.04 | BRL |
| | 9 | 101 | 0.001264 | 4.2325E-10 | 0.05 | BRL |
| | 10 | 143 | 0.001790 | 2.9894E-10 | 0.03 | 7.0 |
| | 11 | 36.2 | 0.000453 | 1.1809E-09 | 0.13 | 5.0 |
| | 12 | 130 | 0.001627 | 3.2884E-10 | 0.04 | 5.0 |
| | 13 | 300 | 0.003755 | 1.425E-10 | 0.02 | 5.0 |

BRL- Dissolved silver concentration is below reporting level

FIG. 11

STUDY 2: Silver concentration calculated from solubility product of AgBr.)

| Spa Study | Week | Bromide (ppm) | Bromide (mol/L) | Calculated Silver (mol/L) | Calculated Silver (ppb) | Actual Silver (ppb) |
|---|---|---|---|---|---|---|
| 2<br>DMH added | 1 | 26 | 0.000325 | 1.6442E-09 | 1.18 | BRL |
| | 2 | 90 | 0.001126 | 4.7498E-10 | 0.05 | BRL |
| | 3 | 74 | 0.000926 | 5.7768E-10 | 0.06 | BRL |
| | 4 | 59 | 0.000738 | 7.2455E-10 | 0.08 | BRL |
| | 5 | <10 | NA | NA | NA | 5.0 |
| | 6 | 64 | 0.000801 | 6.6795E-10 | 0.07 | 6.0 |
| | 7 | <10 | NA | NA | NA | BRL |
| | 8 | <10 | NA | NA | NA | 5.0 |

BRL- Dissolved silver concentration is below reporting limit

FIG. 12

(STUDY 3: Silver concentration calculated from solubility product of AgBr)

| Spa Study | Week | Bromide (ppm) | Bromide (mol/L) | Calculated Silver (mol/L) | Calculated Silver (ppb) | Actual Silver (ppb) |
|---|---|---|---|---|---|---|
| 3<br>DMH added | 1 | NA | NA | NA | NA | BRL |
| | 2 | <10 | NA | NA | NA | BRL |
| | 3 | <1 | NA | NA | NA | BRL |
| | 4 | <5 | NA | NA | NA | BRL |
| | 5 | <50 | NA | NA | NA | 5.5 |
| | 6 | <10 | NA | NA | NA | 5.0 |
| | 7 | 57 | 0.00071 | 7.50E-10 | 0.081 | 5.0 |
| | 8 | 5.3 | 0.00007 | 8.07E-09 | 0.870 | 6.0 |
| | 9 | 44 | 0.00055 | 9.72E-10 | 0.105 | 6.5 |

BRL- Dissolved silver concentration is below reporting limit

WATER TREATMENT

CROSS REFERENCE TO RELATED APPLICATIONS

This application claims is a continuation-in-part of the following: U.S. application Ser. No. 12/315,285 filed Dec. 2, 2008 now U.S. Pat. No. 7,875,191 which is a continuation of application Ser. No. 11/999,654 filed on Dec. 6, 2007, now U.S. Pat. No. 7,501,607 which is a division of application Ser. No. 10/928,668 filed on Aug. 26, 2004, which is now U.S. Pat. No. 7,347,934; U.S. application Ser. No. 12/386,109 filed Apr. 14, 2009 which is a continuation in part of U.S. application Ser. No. 12/001,354 filed Dec. 11, 2007 provisional application No. 61/126,105 filed on May 1, 2008, provisional application No. 60/878,016 filed on Dec. 29, 2006; and U.S. application Ser. No. 11/648,743 filed Dec. 29, 2006 titled Control System which claims priority from provisional application Ser. No. 60/757,198 filed Jan. 6, 2006.

FIELD OF THE INVENTION

This invention relates generally to water systems sanitized with a halogen and, more specifically, to a system for safely controlling the bacteria levels in a body of water such as a pool or spa, wherein a halogen generator in conjunction with a compound contain a hydantoin ring and a source of metal ions may be used to maintain the halogen as much as 50% less than the halogen minimum levels normally required to safely control the bacteria levels in the pool or spa.

STATEMENT REGARDING FEDERALLY SPONSORED RESEARCH OR DEVELOPMENT

None

REFERENCE TO A MICROFICHE APPENDIX

None

BACKGROUND OF THE INVENTION

Contained bodies of water where a person immerses himself or herself partly or wholly in the body of water can be found in swimming pools, spas, hot tubs, jetted tubs as well other containers. Generally, the person immerses his or her body partially or wholly in the body of water in order to obtain the effects of the water. In order to make the body of water safe for body contact it is necessary to kill harmful microorganisms in the water such as bacteria which can be done by dispensing antibacterial materials into the water. These type of water characteristics can be referred to as water safety characteristics. In addition, from time to time other water characteristics of the body of water, such as water comfort characteristics are adjusted. For example, the water temperature may be changed or in some cases the pH of the water may be adjusted sometimes both for safety purposes and for the comfort of the water user.

In general, a pump circulates the water in a container so as to provide a body of water with uniform water characteristics as well as to remove unwanted materials or debris from the water. During the circulation of the water dispensable materials such as minerals or other ion yielding materials can be controllable dispensed into the water through either inline dispensers or floating dispensers to control the microorganisms in the water. Other water characteristics such as a water temperature can be controlled by a heating or cooling the water as it flows through a heat transfer unit. In either case the water characteristics whether safety or comfort characteristics can be changed to make the water suitable and safe for the user.

While water characteristics in the containers have been periodically monitored and controlled by adding dispensable material to the water a feature of the invention is that the water characteristics, such as water comfort characteristics and water safety characteristics, can be monitored and controlled on-the-go. This allows the water characteristics to be maintained within close ranges which can make a users recreational experience in the water not only more comfortable but also insure that the water does not contain harmful organisms.

The invention described herein is well suited to use with small recreational water systems such as pools, spas, hot tubs or the like either as an after market item in those systems have an existing circulation system it can be introduced during the manufacture of the pools, spas, hot tubs or the like.

The concept of treating water with a source of metallic ions to kill bacteria in a body of water is known in the art. A metallic ion such as a silver ion is an effective sanitizer for a body of water including recreational water such as swimming pools, spas, jetted tubs or the like and is a preferred material because it is generally easier and safer to use than other known sanitizers. A further advantage of using silver ion as a sanitizer is that silver ion minimizes the need for pH adjustment of the body of water. However, if the concentration of metallic ions such as silver ions in a body of water is too low the ability to kill microorganisms is reduced or lost. On the other hand if the concentration of metallic ions such as silver ions is too high it can be harmful to those who use the body of water. Thus when silver ion is used as a disinfectant in a body of water one generally want to maintain the concentration of the silver ion in an effective range to kill microorganisms.

Traditionally, the sources of metallic ions used to kill bacteria in recreational water have been limited to metallic ion donors that are readily soluble in the recreational water in order to maintain an effective concentration of the sanitizers in the body of water. Silver chloride (AgCl), for example, has been a commonly used bactericide for releasing silver ions into the body of water to effectively kill microorganisms. Sodium bromide has also been known to be used with silver chloride to provide an additional and alternative water disinfection system.

In order to reduce the level of halogen in a body of water and keep the water sanitized multiple sanitizers have been used in conjunction with a halogen, for example sales literature suggests chlorine levels may be may be kept in the range of 0.5 ppm to 1 ppm if used with multiple sanitizers that include multiple metal ion sources of silver, copper and zinc. In contrast, to the afore described need for multiple sanitizers to keep the body of water in a sanitized condition when halogen levels are as low as 0.5 ppm the invention described herein allows one to use even lower levels of halogen with only a single sanitizer.

One of the problems associated with the use of silver as a sanitizer for killing microorganisms is that silver has a tendency to complex with other compounds and become increasingly insoluble thereby reducing the effective microorganisms killing ability of the silver as a sanitizer. For example, it would not be anticipated that silver chloride when used in combination with sodium bromide would be an effective disinfectant system because of the combination's tendency to form insoluble bromide crystals, which are not believed to be biologically active in aqueous environments. However, it has been discovered that if silver forms a complex with hydantoins, the silver will remain soluble to a higher degree thereby retaining the silver's antimicrobial activity.

SUMMARY OF THE INVENTION

The invention comprises a system for controlling bacteria in a body of water such as a pool or spa by using a halogen in combination with a metal ion source and a compound containing a hydantoin ring wherein the level of halogen is as much as 50% less than a minimum halogen level normally required to maintain the bacteria levels in the body of water at acceptable levels when only a halogen and a source of silver ions are used to control the bacteria.

DESCRIPTION OF THE PREFERRED EMBODIMENT

Figures 1, 2:
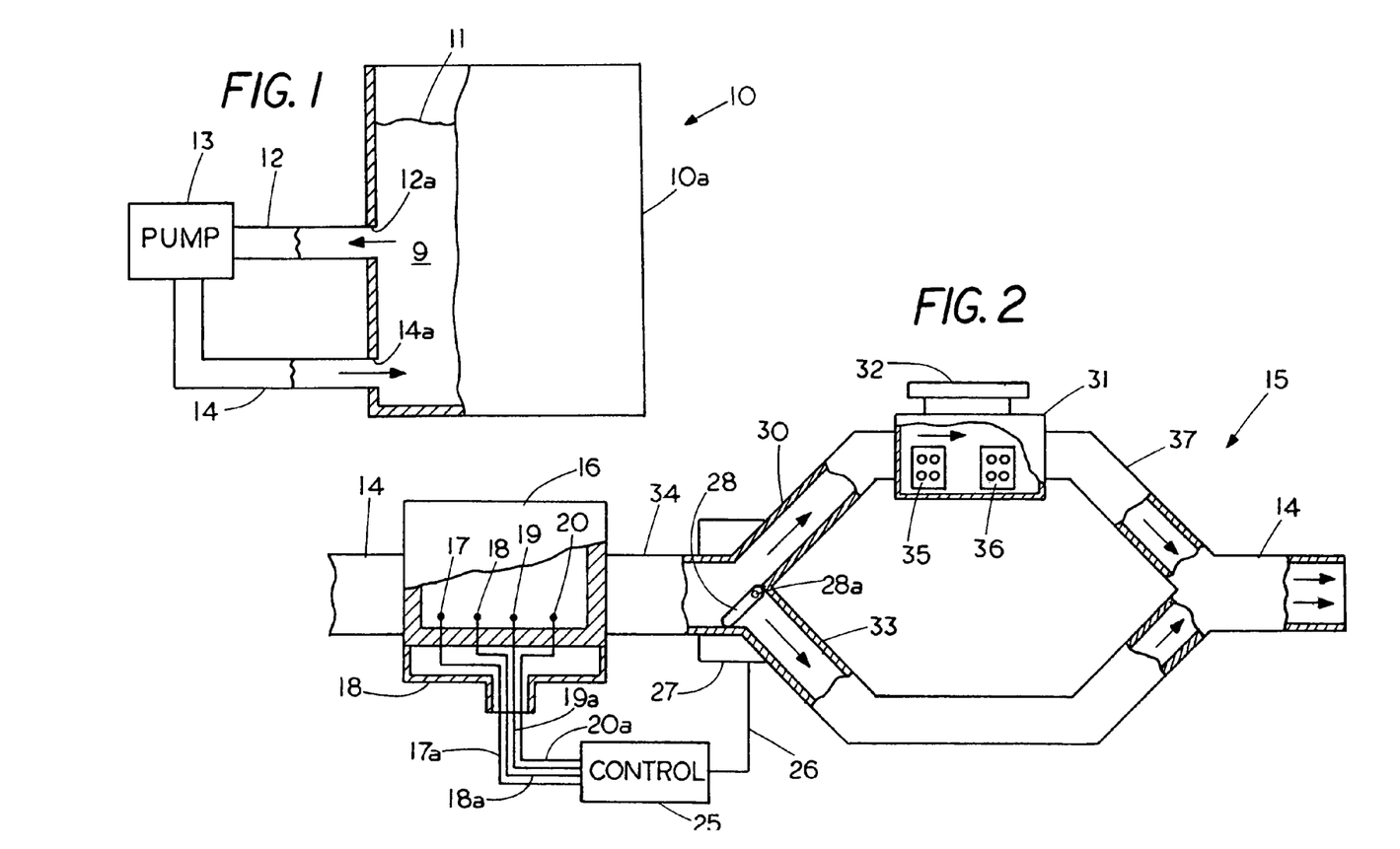
FIG. 1 is a partial cutaway view of a container with a circulation pump.
FIG. 2 is a partial cutaway view of a control system that can provide on off flow or proportional flow through the dispensers.

FIG. 1 shows a partial cutaway view of a system 10 with a container 10a having a water circulation system including a pump 13, an inlet 12a, an inlet line 12, an outlet line 14 and an outlet 14a that circulates fluid to and from container 10 to maintain the water in a user-friendly condition. A filter, not shown, removes any debris from the water during the circulation process. These types of system are particularly well suited for use with recreational waters that are found in swimming pools, spas, hot tubs, jetted tubs or foot baths, which humans immerse themselves partially or wholly therein, since the systems can maintain proper levels of sanitizers such as halogens and metal ions.

In order to provide not only a safe water environment but also a comfortable water environment a number of water comfort characteristics and/or water safety characteristics need to be maintained. For example, the safety of the water needs to be maintained by controlling the level of harmful microorganisms in the water. In addition, other water characteristics such as temperature, pH and salinity of the water should be maintained at the proper levels to provide a comfortable body environment. In some cases the water characteristics can be considered comfort characteristics and in other cases the water characteristics have a direct affect on the safety of the water. In addition, some of the water characteristics can affect other water characteristics. For example, the rate of dissolution of the antimicrobial material can be affected by the temperature of the water as well as the salinity of the water. Because of the potential interrelationship of the various water characteristics the control system described herein provides for automatically maintaining a number of water characteristics within suitable ranges without intervention by the user. The control system is well suited for use with dispensing materials such as a mineral dispenser sold by King Technology of Hopkins Minn.

Figures 3, 4:
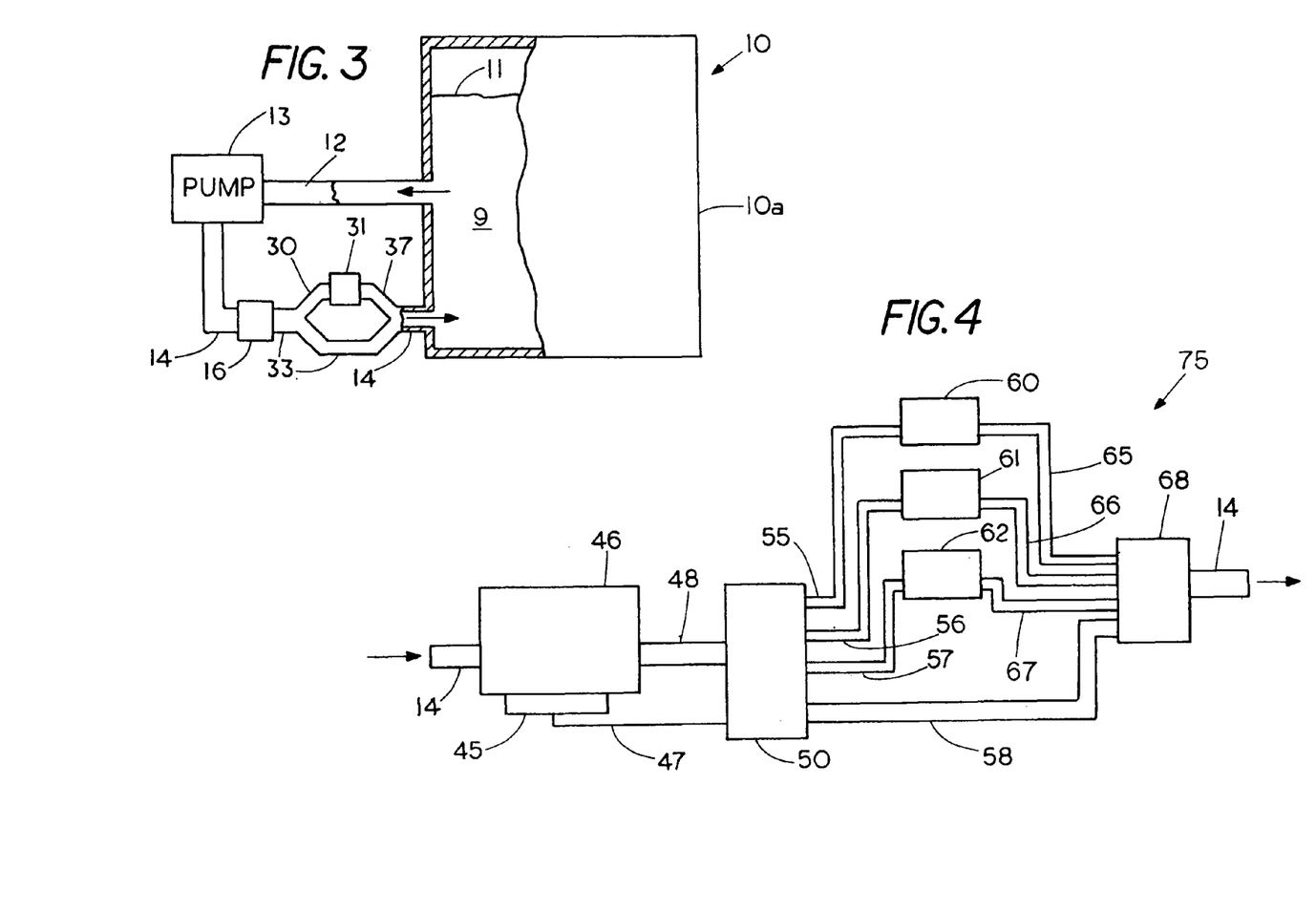
FIG. 3 is a partial cutaway view of the control system of FIG. 2 spliced into the circulation system of FIG. 1.
FIG. 4 is an alternate embodiment of a control system that monitors and controls various comfort and safety characteristics of a body of water.

FIG. 2 shows a partial cut away view of an inline automated on-the-go control system 15 that includes both a water characteristic monitoring unit 16 and a dispensing unit 31 that can be attached to the circulation system of FIG. 1. FIG. 3 shows how the on-the-go control system 15 can be mounted in the outlet pipe 14 of the water circulation system of FIG. 1 to provide both on/off control as well as proportional control of water through the dispenser cartridges 35 and 36.

The control system 15 is suitable for attachment to the water system 10 during manufacture of the water system or as an after market item. Briefly, control system 15 includes a monitor unit 16 that has a first end which is secured to an outlet pipe 14 and a second end secured to pipe 34. Located in monitor unit 16 and upstream of the dispensers 35 and 36 are a set of four different water comfort and water safety sensors 17, 18, 19 and 20. For example, the sensors could be a salinity sensor, a pH sensor, a temperature sensor and a microorganism sensor. Sensor 17 connects to control station 25 through a lead 17a. Similarly, sensor 28 connect to control station 25 through a lead 18a, a sensor 19 connects to control station 25 through a lead 19a and sensor 20 connects to control station 25 through a lead 20a. Sensors, for measuring the above water characteristics are known in the art and are not described herein. While four sensors are shown in monitor unit 16 more or less sensors could be used depending on the number of water characteristics that need to be monitored.

As water flows past the sensors the control station 25 receives the on-the-go signals from the sensors 17, 18, 19, and 20. The control system which can be a processor and hardware that develops a control signal based on the measurements of the sensors and reference levels in the processor. The control system 25 has an output lead 26 that connects to a valve 27 that contains a diverter plate 28. The control signal operates a motor, not shown, that rotates diverter plate 28 into a position to either partially or completely block off one or the other of branch pipes 30 and 33, thus providing analog or proportional control of the water flow or if flow is blocked off completely an on off control of fluid flow threrethrough. While a diverter plate is shown other types of devices may be used to control and regulate the flow of water through the dispensers, for example solenoid valves.

Pipe 30 connects to an inlet side of housing 31, which has a removable cover 32 therein with a first dispenser 35 and a second dispenser 36 located in housing 31. Dispenser 35 and 36 are of the type where the flow area through the dispenser can be increased or decreased by opening and closing ports in the dispenser to limit the flow through the dispenser and thereby control the release of dispersant from the dispenser. An example of such a dispenser where the flow area can be changed is shown in U.S. Pat. No. 7,059,540 and is herby incorporated by reference. Thus with the present invention each of the flow through areas in the two dispensers 35 and 36 can be selected to obtain a desired dissolution rate or dissemination rate for the material contained within the dispenser. Thus, in the embodiment shown at least two dispensers 35 and 36 are used wherein at least one or both of the dispensers one can change the amount of water flowing through the dispenser by controlling the port size in the dispensers. Thus materials, which are dissolved at different rates, can be placed side by side in the single fluid stream flowing through the housing 31. A return pipe 37 connects to an outlet side of housing 31 and joins with branch pipe 33, which connects to return pipe 14. A second branch pipe 33, which acts as a bypass is located in a parallel condition but contains no housing for cartridges, also connects to pipe 14.

In operation of the control system 15 of FIG. 2 water enters pipe 14 and flows past the sensors 17, 18, 19, and 20. In response to the water characteristics the sensors send a signal to the control station 25, which generates a control signal that controls the rotational position of diverter plate 28 in control valve 27. By controlling the position of diverter plate 28 one can direct more or less water through the dispenser housing 31 to thereby provide for on-the-go adjustment of the water characteristics without shutting off the flow of water past the sensors in the monitoring unit. For example, if sensor 17 indicates the level of water borne microorganisms, such as bacteria, is to high one needs to direct more water through the pipe 30 and through the dispenser 35 in the housing 11 in order to raise the level of antibacterial material in the water. If the dispensers in the dispenser housing 31 contains dispensers with minerals or other ion yielding materials one can increase the water flow through dispenser housing 31 to increase the concentration of metal ions such as the silver ion in the water. A feature of the invention is that the condition of bacteria in the water can be monitored continually by sensor 17. Once the bacteria in the container 10 reaches the proper level the control station 25 generates a signal to rotate valve 28 in a clockwise direction to direct the stream of water partially into pipe 30 and partially into bypass pipe 33. Consequently, the water flowing through bypass pipe 33 bypasses the dispenser 35 and dispenser 36 in housing 31. With the decrease in flow though housing 31 and the dispensers 35 and 36 the level of material dispensed into the water decreases. At the same time the volume of circulation of the water in the container can be maintained since the water is diverted from one branch pipe 30 to the other branch pipe 33 or vice versa. That is the rate of water flowing through the pump 13 and back into the container 10 can be maintained with while the water comfort characteristics and the water safety characteristics can be adjusted on-the-go by smoothly directing more or less water through the dispensers holding the dispensable materials. While the water characteristics can be controlled without maintaining a continuous flow the use of this feature allows one to use an existing water circulation system without impacting the circulation of the system. Thus a feature of the invention shown in FIG. 2 is a system with a bypass pipe 33 and a branch pipe 30 with a housing 31 for retaining the dispensers 35 and 36 therein and a diverter valve 27 having a diverter 28 for directing water through either the branch pipe or simultaneously thorough both the bypass pipe or the branch pipe to provide simultaneous control of four sensed parameters with only two dispensers.

FIG. 4 shows an alternate embodiment of the control system 75 that can be fitted into the circulation system shown in FIG. 1. The control system 75 is similar to the control system 15 and includes an inlet pipe 14 that connects to a monitor unit 46 that includes a control station 45 that connects to a diverting chamber 50 containing a set of rotateable valves which are identical to the rotateable valve 28 shown in FIG. 2. A pipe 48 connects to monitor 46 to receive the water that flows though monitor unit 46 and direct the water into housing 50. Housing 50 includes four outlet pipes 55, 56, 57 and 58 that are located in parallel to each other. Outlet pipe 55 directs water though housing 60 and pipe 65 directs the water into plenum chamber 68. Outlet pipe 61 direct water into housing 61 and pipe 66 directs the water into plenum chamber 68 and similarly outlet pipe 57 directs water to housing 62 and pipe 67 directs the water into plenum chamber 68. A fourth outlet pipe 58 connects housing 50 directly to a plenum chamber 68. Plenum chamber 68 receives the water from the various pipes and directs the water into the return pipe 14. As can be seen in FIG. 4 the water discharging from housing 50 includes four separate flow paths, one of which is a by pass and the other three contain dispensers that can separately dispense material into a fluid stream and then can combine the fluid streams with each other so that the dispersant can be mixed before being sent into the body of water to be conditioned.

The housing 50 includes multiple control valves with each of the control valves positioned to open or partially close the amount of water flowing into the respective pipes 55, 56, 57 or 58.

The system of FIG. 4 differs from the system of FIG. 3 in that the housing 60 contains a single material that can affect a water characteristic. Thus, the control of the water and safety characteristics can be made independent of each other. That is, the flow through dispenser housing 60 can be shut off without affecting the flow to dispenser housing 61 or 62. Similarly, the dispenser housings 60, 61 and 62 can be shut off and fluid allowed to flow through bypass pipe 58 and back into the outlet pipe 14. In each system the water characteristics can be monitored on-the-go and the signals developed can be used to increase, decrease or maintain the flow through one or more pipes in order to maintain the water characteristics within a suitable range.

Figure 5:
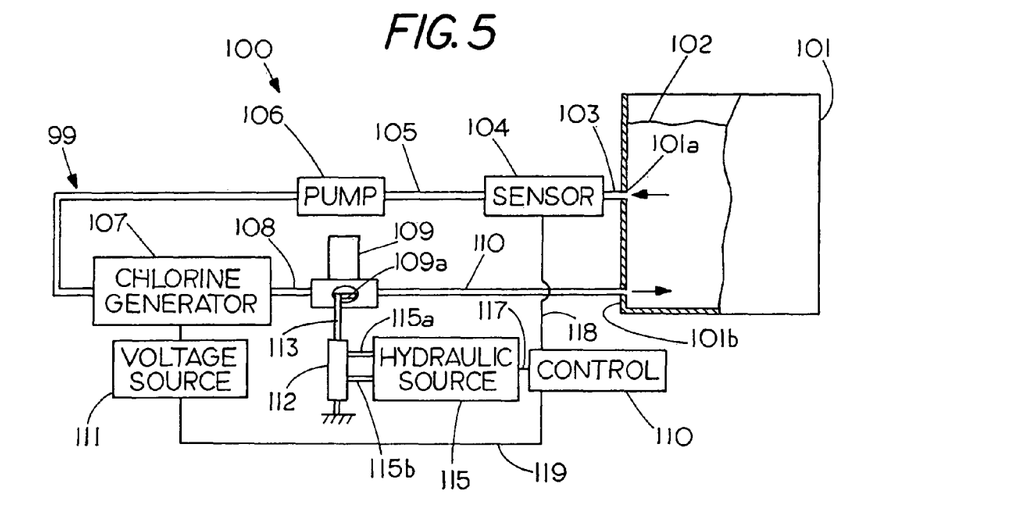
FIG. 5 shows a system for automated analog control of the dispensing materials for a body of water.

FIG. 5 shows a cutaway view of a proportional or analog control system 100 that can be coupled into an existing fluid circulation system as an after market device or, if desired, can be included in the manufacture of a water container and fluid circulation system. It is believed that the on/off type of controls for water systems wherein the control system intermittently stops the dispensing when a measured water characteristic exceeds a specified range may be unsuitable under certain conditions. Generally, in on/off systems the dispensers in the system dispense when the measured water characteristic is below a certain level which can produces abrupt increases in the delivery of dispensing material to the body of water. Conversely, when the measured water characteristic is below a above a predetermined level the dispenser is such off. It is believed that such delivery can produce delays in maintaining the water characteristics at the proper level. In addition, if two or more water characteristics are measured and controlled it is believed it can make it difficult to maintain the proper water characteristics in the container since the level of one water characteristic can affect the effectiveness of another water characteristics. When the container is a smaller body of water such as found in home pools or spas it can result in delays in bringing the water characteristics to the proper level.

Figure 6:
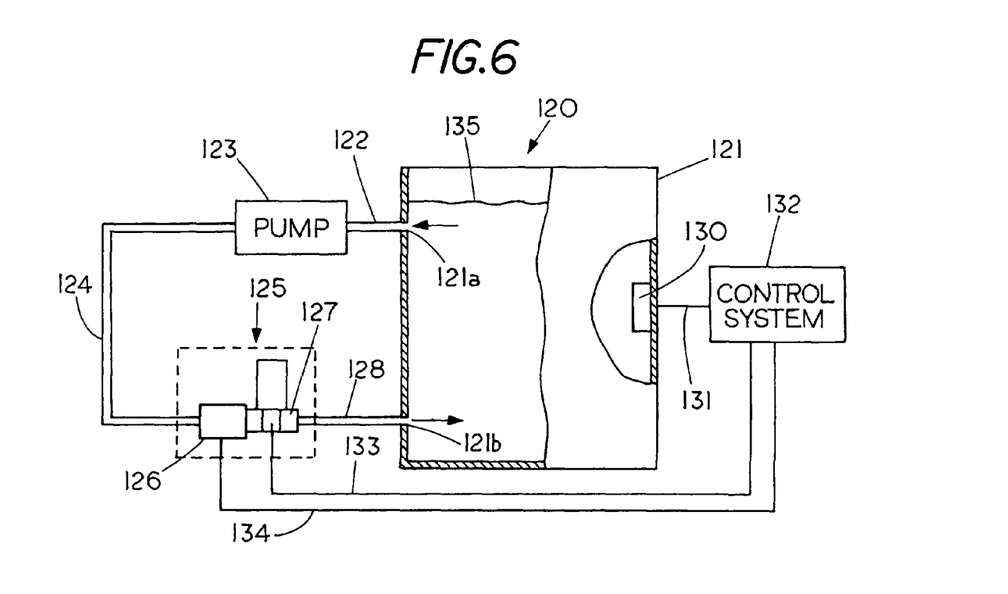
FIG. 6 shows an alternate embodiment of the analog system of FIG. 6 wherein the dispensing units have been spliced into an existing circulation line.

The control system of FIG. 5 and FIG. 6 can provide an analog control system that instead of abruptly turning the system on and off can smoothly changes the dispensing rates to maintain the proper water characteristics. Since the analog rate of dispensing material is changes smoothly it can eliminate a local region in the body of water where the water characteristics may be extremely high because a dispensing material has been rapidly added to the water to bring the water characteristics of the entire body of water to the proper level. However, if desired the system can be operated in an on off manner enabling an operator to have the benefit of an analog or proportional system as well as an on off system.

The system of FIG. 5 shows an analog control system 100 with a container 101 having a body of fluid, such as water 102, therein and a conventional fluid circulation system 99 with water characteristic sensors 104 and dispensers 107 and 109 connected to the circulation system 99. More specifically, the fluid circulation system 99 includes a container outlet 101a connected to a water pump 106 that draws water therein through conduit 103, water characteristic sensors 104 and conduit 105. The circulation system pump 106 then directs the water through a chlorine or salt generator 107, which can generate and maintain a constant level of chlorine ions in the body of water, a conduit 108 and an inline dispersal valve 109, which can releases an antibacterial materials or sanitizers such as silver ions, and a conduit 110 that connects to container inlet 101b to bring the water back to the container 101.

A feature of the system of FIG. 5 is that both the chlorine generator 107 and the inline dispersal valve 109 can be spliced into a circulation line 99 of an existing system 100. In addition, the water characteristic sensors 104, which can measure one or more water characteristics is also shown spliced into the circulation line; however, if desired, the sensors 104 could also be mounted in the container 101 to monitor the water characteristics in the container rather than in the incoming water in the fluid circulation system.

In operation of the system of FIG. 5 a water characteristic is measured by sensors 104, for example sensors 104 can monitor the chlorine level in water 102. In response to the level of chlorine in the water a signal is sent to control 110 which in turn can change the voltage supplied to chlorine generator 107. By changing the output of the voltage source 111 that powers chlorine generator 107 one can change the chlorine output and by increasing or decreasing the voltage without shutting off the voltage one can smoothly and gradually change the chlorine output to avoid local regions of high chlorine concentrations. Thus, by changing the voltage to the chlorine generator 107 one can allow the fluid to be continuously circulated i.e. without interruption, through the chorine generator 107. That is, if the chlorine ion sensor in water characteristics sensor 104 detects the chlorine level is deviating from the desired level the voltage to the chlorine generator can be increased to increase the release of chlorine ions or if the chlorine level is becoming to high the voltage to the salt generator can be decreased thus reducing the chlorine output. In either case the control of power to the chlorine generator allows one to closely control the release of chlorine ions into the water without having to change the flow of water through chlorine generator. Thus, in one example one can provide an analog system that can continually and smoothly control the output of the chlorine generator without the need for periodic manual adjustment. Devices wherein the voltage of a chlorine generator is manually selected to control the dispensing of chlorine items manufactured and sold by American SPS of Altamonte Springs, Fla. In still other examples one may maintain the level of chlorine through digital control.

In order to maintain a body of water such as a pool or a hot tub in a sanitized condition when using only a halogen sanitizer and a single source of heavy metal ions such as silver ions one needs to maintain a minimum level of halogen in the body of water. For example if chlorine is used in conjunction with a source of silver ions it is recommend that the minimum level of chlorine should be 1 ppm. Similarly, if bromine is used in conjunction with a source of silver ions the minimum level of bromine needed to maintain the body of water at a safe level is 2 ppm.

With the above level of sanitizers the body of water becomes safe for human contact. A recommended minimum halogen level for the body of water may vary depending on the tests standards, for example, one known EPA test standard requires the water have no more than 200 cfu of heterotrophic bacteria per ml; no more than one cfu of *Enterococcus* sp. Per 50 ml and no more than one cfu of *Escherichia coli* per 50 ml. The above levels of bacteria are generally consider safe levels of bacteria for bodies of water such as pools and spas and have been approved as such by regulatory governmental bodies such as the EPA.

Another test standard requires that the minimum halogen level be such that (a) an organism count in the recreational body of water of less than 200 organisms per milliliter; (b) a coliform bacteria count in the recreational body of water of less than 2 bacteria per 100 milliliters; and (c) an entercoccal organism count in the recreational body of water of less than 2 entercoccal organisms per 50 milliliters.

To meet the above EPA test standards for the allowable number of harmful organisms in a body of water the minimum recommended halogen level of bromine is 2 ppm or greater and the minimum recommended halogen level of chlorine is 1 ppm or greater if the halogen is used in conjunction with a source of metal ions such as silver ions. If additional sanitizers are used with the chlorine and the source of metal ions the EPA may recommend that the level of chlorine may be as low as 0.5 ppm.

While the test standards may vary in each instance the body of water, which comes into external human contact must be sanitized to kill harmful organisms. The use of a source of silver ions in conjunction with a halogen and a compound containing a hydantoin ring provides a method and composition that kills harmful organisms with reduced levels of halogens without the need to use additional sanitizers.

In one example a chlorine generator, when used with a source of silver ions and a compound containing a hydantoin ring, is set to maintain the level of chlorine in the pool or spa as low as 0.25 ppm, which is as much as 50% to 75% less than the minimum recommended halogen levels to maintain acceptable levels of bacteria in a body of recreational water such as a pool or spa when chlorine and a source of silver ions are used as the sanitizers.

Typically, the chlorine generator of FIG. 5 is set to maintain a minimum chlorine level in the body of water at 1 ppm when used with a dispenser that includes a source of silver ions. Similarly, when a halogen generator, such as a bromine generator is used the bromine generator is set to maintain the level of bromine at 2 ppm when used with a dispenser that includes a source of silver ions.

Typically, a conventional sanitizing system may use only a halogen and a single source of metal ions for microorganism control in a body of water. If the halogen is chlorine, the chlorine level is maintained at a minimum of 1 ppm. If the halogen is bromine the bromine level is generally maintained at a minimum of 2 ppm. If additional sanitizers are used such as multiple sources of metal ions one may be able to reduce the level of halogen such as chlorine in the body of water to 0.5 ppm. In the system described herein one can obtain microorganism control in a body of water by adding a compound containing a hydantoin ring to the body of water containing a halogen and a source of silver ions regardless of whether the compound containing a hydantoin ring has any biocidal properties. For example, if the halogen is chlorine one can obtain microorganism control in a body of water a with a chlorine level as low as 0.25 ppm when the source of metal ions is used in conjunction with a compound containing a hydantoin ring Thus, in the invention described herein the halogen generator can be set to maintain the halogen level in the pool or spa at 50% to 75% less than would be normally required to safely control the bacteria level in the pool or spa when a compound containing a hydantoin ring such as DMH is also used. For example, a chlorine generator can be set to maintain a minimum level of chlorine of 0.25 ppm in the body of water.

The chlorine generator of FIG. 5 can be set to maintain the chlorine level in the body of water between 0.25 ppm and 1 ppm and the dispenser can include a source of silver ions and a compound containing a hydantoin ring such as DMH.

In one example, a cartridge contains a source of silver ions, such as silver chloride, which may be coated onto a carrier using a binder and a hydantoin such as DMH.

To determine if the level of bacteria in the water was acceptable with 0.5 ppm chlorine tests were carried out based on the EPA directive DIS/TSS-12 using over 144 water samples, which were examined for the levels of microorganisms in the water samples. To meet the EPA test requirements for pools and spas at least 85% of the samples had to have no more than 200 cfu of heterotrophic bacteria per ml; no more than one cfu of *Enterococcus* sp. Per 50 ml and no more than one cfu of *Escherichia coli* per 50 ml. The pool studies were carried out at temperatures ranging from 80° F. to 90° F. and the spa studies were carried out at temperatures ranging from 100° F. to 104° F.

It was found that a chlorine concentration as low as 0.25 ppm, when used with a source of silver ions and a compound containing a hydantoin ring met the EPA standards for maintaining safe levels of bacterial in the body of water. Thus the concentration of chorine in the body of water is 50% to 75% less than normally required to safely control the bacteria level in the pool or spa.

While a halogen generator such as a chlorine generator can be used in conjunction with the source of metals ions such as silver ions and a compound containing a hydantoin ring such as DMH one can also use a halogen generator such as a bromine generator with a source of metals ions such as silver ions and DMH to similarly lower the level of bromine in the body of water.

Thus the invention encompass a method of maintaining a body of recreational water in a sanitized condition with use of a halogen and a source of silver ions wherein the halogen is maintained at less than 0.5 ppm if the halogen is chlorine and less than 2 ppm if the halogen is bromine by adding a compound containing a hydantoin ring to the recreational body of water. The level of halogen in the body of recreational water can be maintained with a halogen generator and the sanitized condition may have any or all of the following conditions: (a) an organism count in a recreational body of water of less than 200 bacteria per milliliter; (b) a number of coliform bacteria in the recreational body of water less than 2 organisms per 100 milliliter; or (c) a number of entercoccal organisms in the recreational body of water less than 4 organisms per 100 milliliter.

Thus the sanitizing of the body of body of recreational water such as a pool or spa using a halogen in combination with a metal ion source and a compound containing a hydantoin ring the level of halogen in the body of water can be as much as 50% to 75$ less than is normally minimum required to maintain the bacteria levels in the body of water at acceptable levels when only a halogen and a source of silver ions are used to control the bacteria. The compound containing a hydantoin ring may be either a halogenated compound or an unhalogenated compound.

In one example a chlorine generator, when used with a source of silver ions and a compound containing a hydantoin ring, can be set to maintain the level of chlorine in the pool or spa between 0.25 ppm and 0.5 ppm, which is as much as 50% to 75$ less than normally required to maintain acceptable levels of bacteria in the pool or spa when only chlorine is used with the source of silver ions.

System 100 also includes a dispensing valve 109 wherein a dispersant is placed in the dispensing valve and a portion of the water flowing through the valve is directed through a chamber in the dispensing valve to deliver the dispersant therein to the body of water. A dispensing valve wherein the setting on the valve is manually adjusted is sold by King Technology of Hopkins Minn. and is more fully described in U.S. Pat. No. 6,544,415.

In the system 100 the dispensing valve 109 has been automated by connecting the rotateable handle 109a to an extendible ram 113 of a two-way hydraulic cylinder 112. The other end of hydraulic cylinder 112 is pivotally mounted on support 114. A hydraulic source 115 has one line 115a connected to one side of the two way hydraulic cylinder and a second line 115b to the other side of the two-way hydraulic cylinder to provide analog control of the rotateable valve through extension and contraction of extendible ram 113. The hydraulic source 115 is connected to control 110 by lead 117.

In operation of the system the control 110, which can be a processor, receives a signal from the water characteristic sensor 104 and in response thereto sends a signal to the hydraulic source 115 to either rotate or maintain the rotateable handle 109a in the same position. For example, if the water sensor 104 detects that the level of metal ions is to low more metal ions can be dispensed into the fluid line by sending a signal to hydraulic source 115 that will proportional extend ram 113 to thereby rotate valve handle 109a to increase the rate of dispensing of metal ions into the fluid. Since the rate of dispersant can be changed without having to shut down the dispensing unit one can smoothly adjust the deliver of the dispensing material from the dispensing unit 109.

Thus, a feature of the system 100 of FIG. 5 is that an existing manually adjustable system, which is manually adjusted to increase or decrease the release of antibacterial material, can be adapted to use with the control 110 to provide for continuous on-the-go control of the water characteristics thus ensuring that the water characteristics are maintained as closely as possible to the proper safety and comfort levels without having to abruptly shut off the dispensing units thus minimizing effects of one water characteristic on another water characteristic.

FIG. 6 shows an alternate embodiment of a control system 120 when a container 121 includes a circulation system that has a pump 123 that takes water at inlet 121a, drawing it through conduit 122 and directs it through conduit 124 and into dispensing unit that has been spliced into return line 128 which delivers the circulation fluid to the container through outlet 121b. In the system of FIG. 6 the water characteristic sensors 130 are mounted in the body of water and the measured level of water characteristic is sent via lead 131 to control system 132, which in turn, sends a control signal to chlorine generator 126 through lead 134 and to dispensing valve 127 through lead 133. The signal delivered to chlorine generator 126 and to dispenser valve 127 are analog so that the deliver of material can be changed without having to shut down the deliver of dispersant into the water. A feature of the system of FIG. 6 is that the dispenser can be spliced directly into a circulation line of an existing system.

Figure 7:
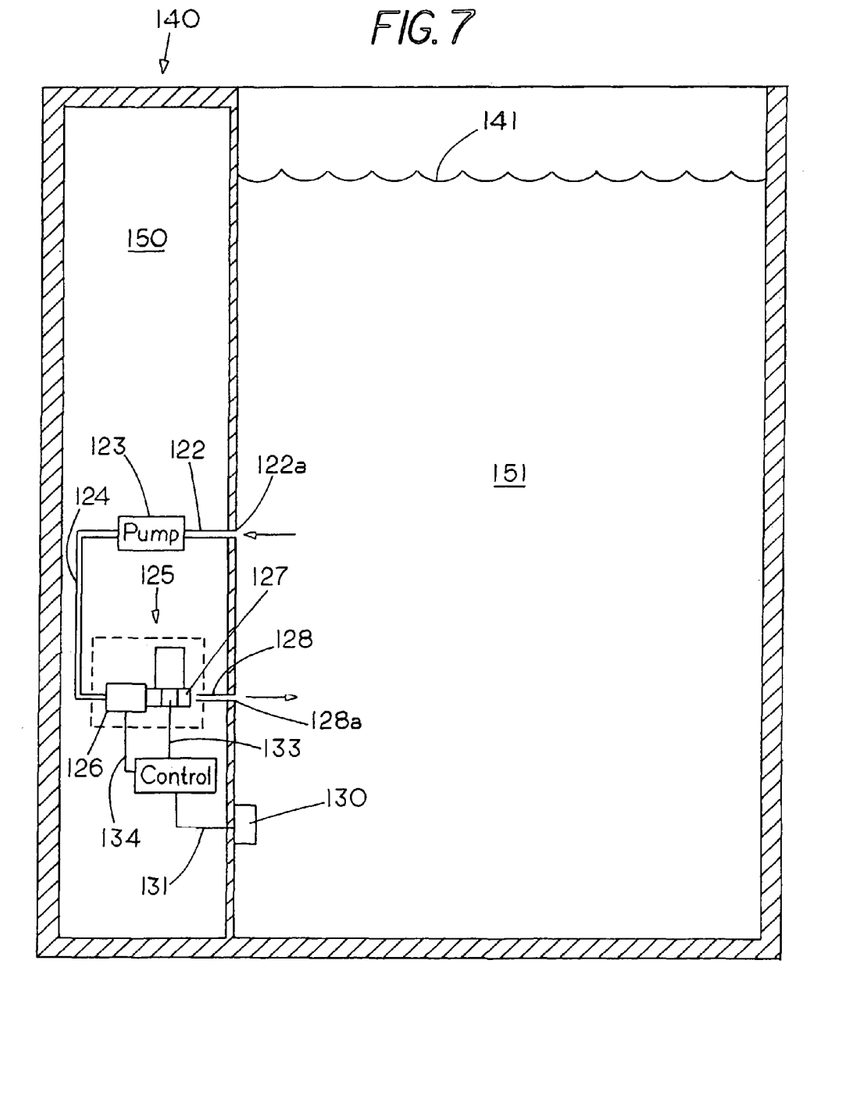
FIG. 7 shows a system with a halogen generator mounted to a body of recreational water.

FIG. 7 shows a container 140 containing a body of recreational water 141 located in compartment 151 and a halogen sanitized system located in compartment 150. The halogen sanitized system, which may be an after market item, includes a circulation system that has a pump 123 that takes water at inlet 122a, drawing it through conduit 122 and directs it through conduit 124 and into halogen generator 126 and dispensing unit 127 that has been spliced into return line 128 which delivers the circulation fluid to the container through outlet 128a. In the system of FIG. 7 a water characteristic sensor 130 may be mounted in the body of water and the measured level of water characteristic is sent via lead 131 to control system 132, which in turn, sends a control signal to chlorine generator 126 through lead 134 and to dispensing valve 127 through lead 133. The signal delivered to chlorine generator 126 and to dispenser valve 127 may be analog or digital so that the deliver of sanitizer to the body of water can be changed without having to shut down the delivery of dispersant into the water. A feature of the system of FIG. 7 is that the dispenser can be spliced directly into a circulation line of an existing system to enable control of the sanitizing using a halogen generator. While a halogen generator is shown it is envision that other methods of maintaining the level of halogen may be used. An advantage of the use of a halogen generator is that the halogen generator can be quickly set to deliver the proper amount of halogen.

While the control system has been shown in use with a chlorine generator and a dispersal valve that delivers metal ions the control system can be used to smoothly control other water characteristics of the body of water. For example, the pH of the body of water is another water characteristics that can benefit from the control system. Thus the system is shown uses a control signal to increase, decrease or maintain the flow as well as other water characteristics.

A compound having a hydantoin ring including unhalogenated hydantoins, such as 5,5-dimethylhydantoin (DMH), has the qualities to interact with metal ion donors including silver metal ion donors such as the silver bromide to increase the solubility of the silver bromide in a water environment and aid in the disinfection process. That is, with a silver ion donor in the presence of DMH, the dissolved silver concentrations are higher than anticipated when compared to a control solution without the presence of DMH. The results suggested that DMH interacts with silver to form a soluble complex even if the source(s) of silver are from insoluble salts such as silver bromide, which in some cases may be derived from silver chloride.

In order to verify that the DMH interacts to increase the solubility of extremely insoluble silver, the following tests were performed using either silver chloride or silver bromide as the donor of metal ions in order to demonstrate the enhancement of a silver concentration in a body of water when DMH is used in combination.

Example 1

Silver bromide was initially prepared from a saturated sodium bromide solution, combined with silver nitrate in solution. The yellow precipitate, silver bromide, was than purified by filtration and washing. Additionally, the solid was allowed to dry before use.

A buffer system having a pH of 7.41 was prepared by adding Fisherbrand® potassium phosphate monobasic-sodium phosphate dibasic buffer to 2 Erlenmeyer flasks filled with 1000 ml of purified water. The first flask was treated with 1.12 grams of 5,5-dimethylhydantoin (DMH) and marked solution "D" and the second flask was left untreated and marked solution "C" for control. In regards to the 5,5-dimethylhydantoin (DMH), the 5,5-dimethylhydantoin (DMH) comprised 97% reagent grade was obtained from Aldrich® (CAS No. 77-71-4, Cat. No. D161403-1KG).

After the initial set-up, approximately 0.10 grams of dried silver bromide was introduced into a dialysis tubing (Fisherbrand®, 45 mm, MWCO 12,000-14,000) along with purified water. The ends of the dialysis tubing were clamped to contain the silver bromide and purified water. Next, the outside of the dialysis tubing was rinsed several times to ensure that silver bromide residue was not on the outside of the dialysis tubing. A string was then tied to one clamp, and one tube was introduced into each flask. A magnetic stir bar was used to mix the solutions.

During the period of the test, a 100 ml sample were removed from solution "D" and solution "C" at weekly intervals and analyzed for their pH using Orin Perphect Meter 370 and analyzed for their silver ion concentrations using atomic absorption spectrometry.

Figure 8:
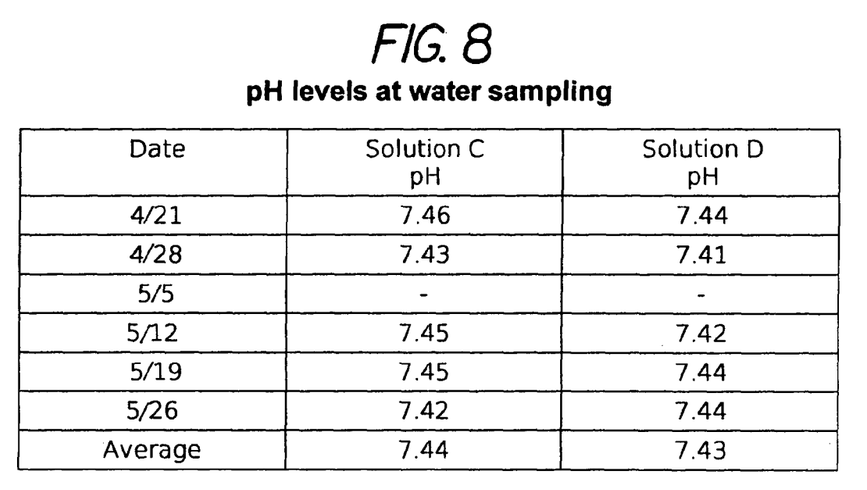
FIG. 8 shows a table of the pH levels of a solution containing DMH and a solution without DMH at weekly time intervals.

FIG. 8 shows a table containing a list of the pH levels obtained from the 100 ml samples for both solution "D" and solution "C" at each of their respective weekly time intervals. It is noted that the preferred pH level for recreational water used in spas, pools, swimming pools, jetted bathtubs and other confined bodies of water is between 7.20 to 7.60 and that the mean value of the pH level measured during the length of the test for both solution "D" and solution "C" was around 7.4, which is within the preferred range.

Figure 9:
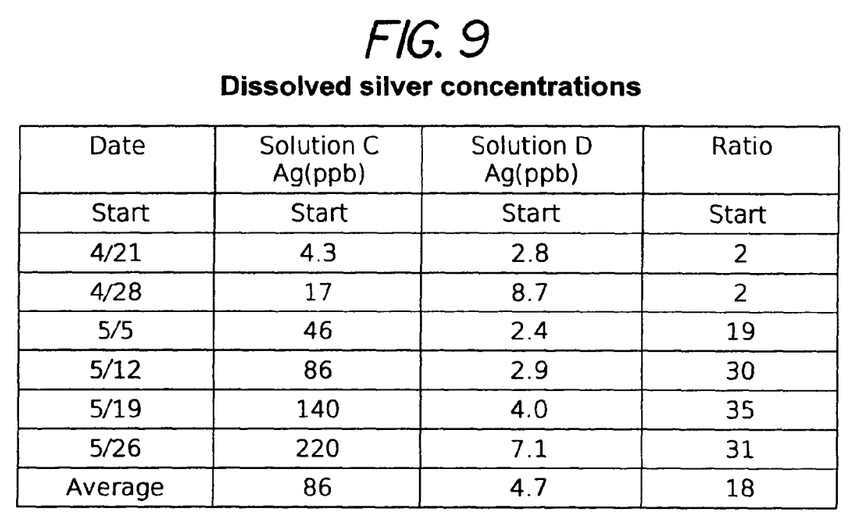
FIG. 9 shows a table of the dissolved silver concentrations of a solution containing DMH and a solution without DMH.

FIG. 9 shows a table containing a list of the dissolved silver concentration, in parts per billion (ppb) obtained from the 100 ml samples for solution "D" and solution "C" at each of their respective weekly time intervals. The average concentration of dissolved silver for solution "D", which contained the DMH, was 86 ppb while solution "C", containing no DMH, had an average concentration of dissolved silver of 4.7 ppb.

A week after the start date, the concentration of dissolved silver for solution D was at 4.3 ppb, while the concentration of dissolved silver for solution C was at 2.8 ppb. By the end of the testing, 6 weeks later, the concentration of dissolved silver for solution D had increase to 220 ppb, while the concentration of dissolved silver for solution C was 7.1 ppb. That is, by the end of the 6 weeks test, the concentration of dissolved silver was at least 30-fold greater in solution D containing the DMH then for solution C containing no DMH.

In summary, the results of the above testing confirmed that in a solution containing silver bromide, the presence of DMH leads to a higher dissolved silver concentrations than compared to a control solution containing silver bromide without the presence of the DMH. These results suggest that DMH interacts with silver to form a soluble complex even if the source of silver comprises an extremely insoluble silver salt such as silver bromide.

Example 2

In the second test, two test spas were used in performing 3 studies to evaluate the potential use of DMH to increase silver solubility in the presence of alternative disinfection systems such as sodium bromide. The first spa used was a 125-gallon Marquis® brand triangle shaped spa having the dimensions 60"×60"×82" with a height of 32" and a water depth of 27"

without bathers. This spa featured 13 jets and one pleated filter cartridge (Unicel 5CH-502), having a filtration area of 50 square feet. The second spa was a 325-gallon Dimension One® brand spa having the dimensions 90"×90"×35.5" with a water depth of approximately 25" without bathers. The Dimension One® brand spa featured 32 jets and two pleated filter cartridges (Unicel 7CH-975), each having a filtration area of 75 square feet. Spa water was maintained between 100° F. (37.8° C.) to 104° F. (40° C.) and was circulated at least 2 hours daily.

In the each of the studies, a reagent grade Dimethylhydantoin (DMH, CAS No. 77-71-4) obtained from Aldrich® with a 97% purity, was used. A concentration of 5 ppm DMH was selected because that amount of DMH can be delivered in the existing King Technology, Inc. Spa Frog® Mineral Cartridge to a 600 gallon spa, the largest volume for the cartridge was designed.

The source of silver ions was obtained from a King Technology Inc. Spa Frog® Mineral Cartridge, which was randomly selected from King Technology Inc.'s production inventories for use in these studies and installed into the in-line system on the spa. These mineral cartridges release silver ions into the spa in the form of silver chloride.

In Spa Studies 1 (FIG. 10) and spa study 2 (FIG. 11), a commercially available sodium bromide disinfectant system (Rendezvous®) was used. With this bromine disinfectant system, the sodium bromide solution is oxidized by the addition of potassium peroxymonosulfate.

For Spa Study 3 (FIG. 12), different sodium bromide disinfecting systems were evaluated in two phases. During the first phase, the commercially available sodium bromide oxidized by the sodium dichloro-s-triazinetroine disinfectant known as Spa Essentials® Brominating Concentrate was used. For the second phase of the spa study reagent grade sodium bromide salt and potassium peroxymonosulfate was used.

During the study, the test spa was filled with fresh water prior to the initiation of each study and the water balanced according to Taylor Technologies Pool & Spa Water Chemistry Manual. The pH was reduced through the addition of sodium bisulfate (pH Down Balancer, GLB, Alpharetta, Ga.) to a range from 7.2 to 8.0. After balancing the spa the King technology, Inc. Spa Frog® Mineral Cartridge was installed into the inline system of the test spa and a source of bromine was added to the spa water.

In Spa Study 1 an amount of DMH was added to the spa water after 7 weeks of silver data had been collected to result in a final concentration of 5 ppm. For Spa study 2, an amount of DMH was added to the spa water after 3 weeks of silver data had been collected to result in a final concentration of 5 ppm, and for Spa Study 3 an amount of DMH was added to the spa water after 1 week of silver data had been collected to result in a final concentration of 5 ppm.

Sodium bromide or brominating concentrate (dichlorostriazinetrione plus sodium bromide) was added to each spa during test intervals. Typically, sodium bromide was activated by oxidation to bromine with potassium peroxymonosulfate. Alternatively, when the brominating concentrate (dichloro-striazinetrione plus sodium bromide) was used, the sodium dichloro-s-triazinetrione oxidized the sodium bromide to make bromine in-situ. Additional water was added to the spa when the water level dropped below the skimmer water returns.

Figure 10:
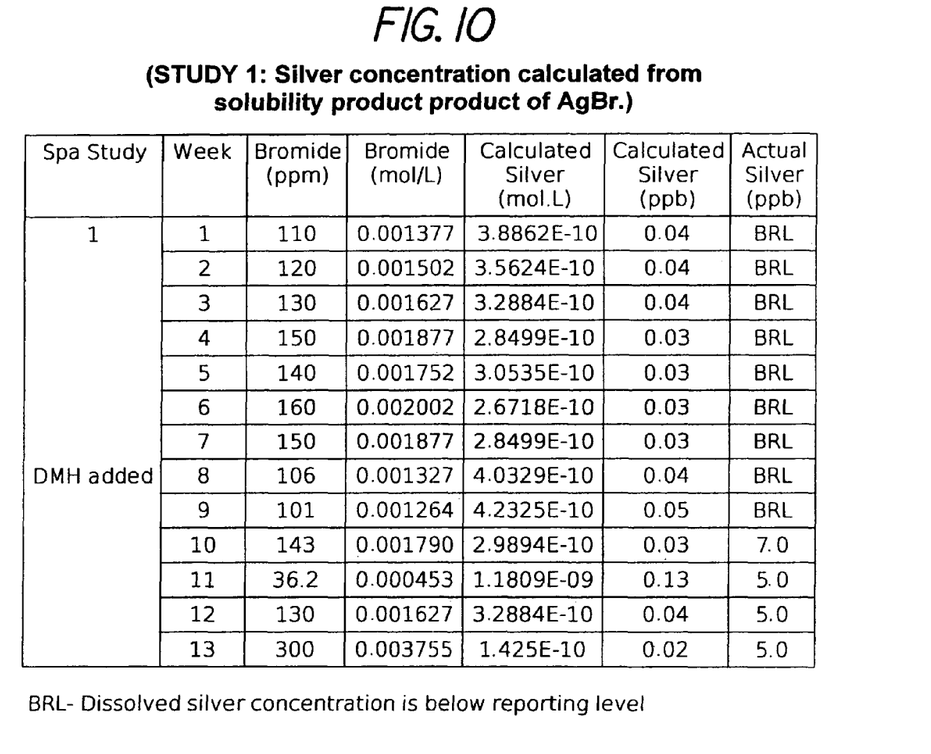
FIG. 10 shows a table containing the test results for bromide and dissolved silver concentration for Spa Study 1.
Figure 11:
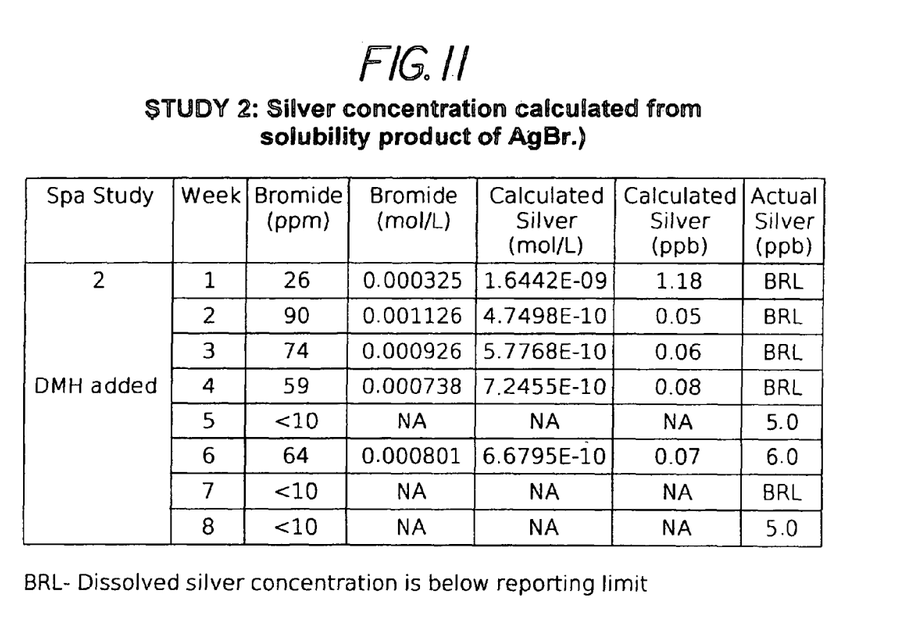
FIG. 11 shows a table containing the test results for bromide and dissolved silver concentration for Spa Study 2.
Figure 12:
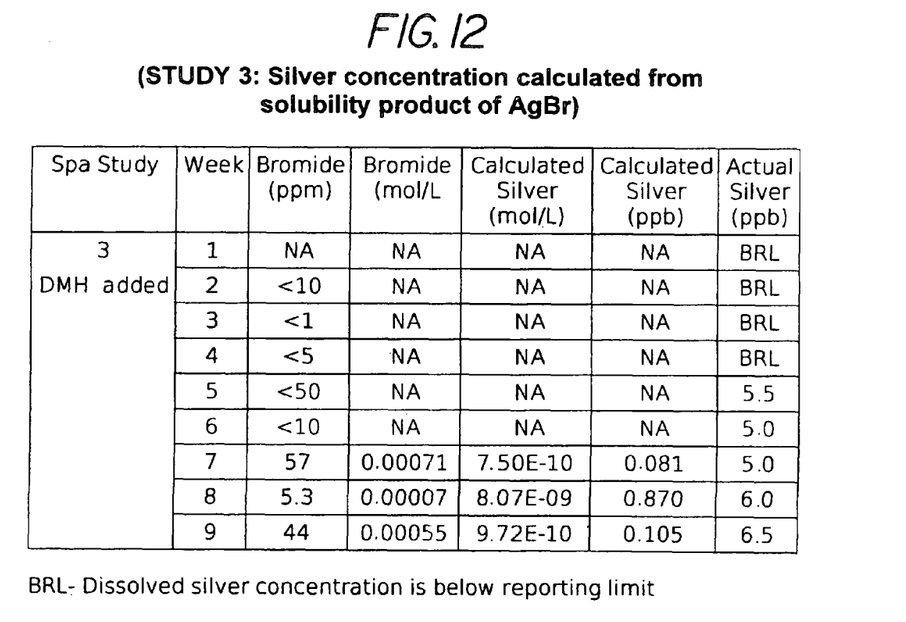
FIG. 12 shows a table containing the test results for bromide and dissolved silver concentration for Spa Study 3.

Chemical tests were performed with water samples obtained from each of the spa for dissolved silver, bromide, and chloride approximately once a week. Bromide was tested to provide a means to calculate the theoretical silver concentration based on the solubility product of silver bromide. The spa water samples were each tested for the bromine, and dissolved silver concentration. Result of the test for bromide and dissolved silver concentration are shown in FIG. 10 for Spa Study 1, are shown in FIG. 11 for Spa Study 2, and are shown in FIG. 12 for Spa Study 3.

Additionally, to maintain the water within the spa total alkalinity, turbidity, and pH were tested and maintained within ranges accepted by the industry. The ideal pH for a spa is 7.20 to 7.60, however wider ranges are acceptable. In the studies, the average pH for Spa Study 1 was 7.51, Spa Study 2 showed an average pH of 7.61, and Spa Study 3 had an average pH of 7.47. These three spa studies were maintained within the ideal pH for a spa.

The International Aquatic Foundation (ANSI/NSPI) recommends a level of total bromine to be between 2.0-4.0 ppm for residential spas with a max of 6.0 ppm. In the studies, the average total bromine concentration measured for Spa Study 1 was 3.74 ppm, the average total bromine concentration measured for Spa Study 2 was 6.56 ppm, and the average total bromine concentration measured for Spa Study 3 was 3.58 ppm.

In regards to the level of silver ions, the King Technology, Inc. Spa Frog® Mineral Cartridge provides silver ions in the form of solid silver chloride (AgCl) distributed over a porous matrix. Water flowing through the matrix comes into contact with the AgCl resulting in the release of soluble silver ions to water. DMH was also released into the water resulting in the formation of ionic-hydantoin structures. It would be anticipated that soluble silver ions would be depleted from spa water through the formation of silver bromide, an insoluble salt. However, as shown in FIG. 10 for Study 1, after the DMH was added to the water in the pool, the actual silver concentrations were higher than the calculated theoretical silver concentration.

The result of Study 1 were further supported in Study 2 and Study 3, shown in FIGS. 11 and 12, which both show that after the DMH was added to the water in the pool, the actual silver concentrations were higher than the calculated theoretical silver concentration. More specifically, once measurable within reporting limits the average measured concentration of dissolved silver for Spa Study 1 was 5.5 ppb. Spa Study 2 had an average measured concentration of 5.33 ppb for dissolved silver and the third Spa Study had a measured concentration of dissolved silver of 3.2 ppb. Referring to FIGS. 10, 11, and 12, the highest observed silver concentration in each spa study was, 7 ppb, 6 ppb, and 6.5 ppb, respectively.

Referring to FIGS. 10, 11, and 12, the results of the three spa studies revealed that before the addition of DMH, dissolved silver concentration was below the official reporting limit of 4.8 parts per billion (ppb). However, around one to three weeks after the addition of a concentration of 5 ppm DMH, silver concentrations in each of the Spa Studies increased above the reporting limit, and were significantly higher than concentrations that would be anticipated based on silver solubility calculations from silver bromide. The above results of Spa Studies 1, 2, and 3 thus supports the finding that the combination of an unhalogenated hydantoin such as 5,5-dimethylhydantoin with a metal ion donor such silver bromide enhances a concentration of the metal ions in the body of water by retaining or increasing the solubility of metal ions from other metal ion donors to retain the antimicrobial activity of the metal ions in the water. Generally, a compound contain a hydantoin ring is added as needed with levels of 5 ppm sufficient to provide enhanced silver ion concentration, however, if the compound containing a hydantoin ring is considered inert one may want to maintain the level of at 10 ppm or more in the body of water. For example if, DMH, which is considered inert, may be normally added to maintain a level of 5 ppm DMH, which is sufficient to provide an enhanced silver ion concentration, however since DMH is considered inert one may want to maintain the level of DMH at 10 ppm or more in the body of water to ensure there is sufficient DMH available at all times.

Because the levels of metal ions in the body of water, such as silver ions, are greater than normally expected the amount of halogen used in conjunction with the source of metal ions, such as silver ions, can be reduced as much as 50% to 75% from existing recommendations while still maintaining the water in a sanitized condition.

Figure 13:
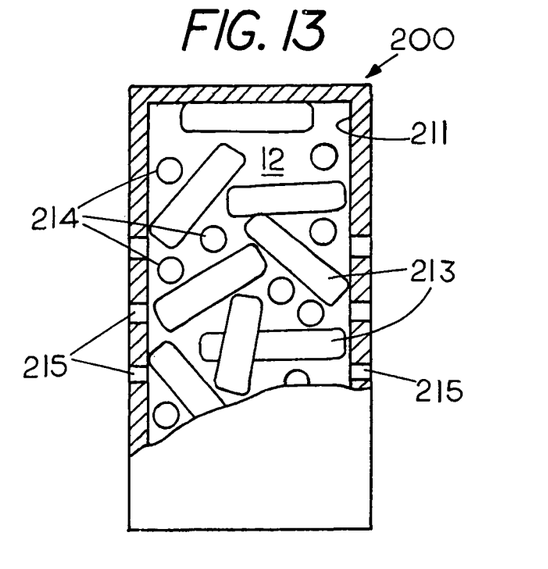
FIG. 13 shows a dispenser having a housing containing a compartment containing DMH and a silver ion donor comprising silver chloride therein.
Figure 14:
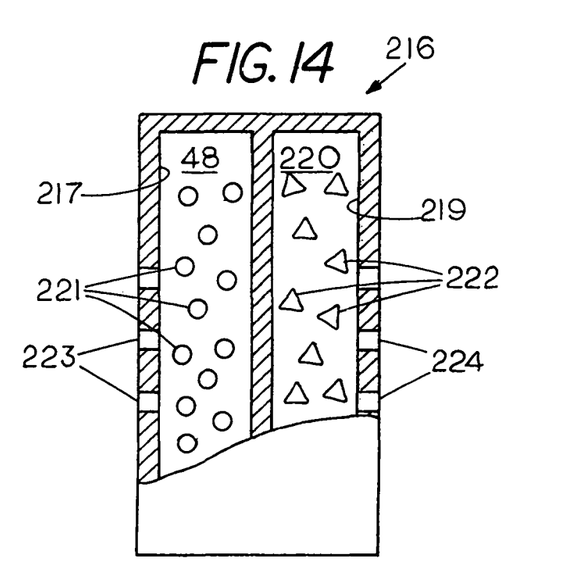
FIG. 14 shows a dispenser having a first housing containing a compound containing a hydantoin ring and a second housing containing silver ion donor comprising silver chloride therein.

Referring to FIG. 13 and FIG. 14, FIG. 13 shows an example of a dispenser 200 having a housing 211 containing a compartment 212 therein. Located in compartment 212 is a source of DMH 213 and a bactericide comprising a silver ion donor such as silver chloride 214. A set of openings 215 allows water access to compartment 212 and to the source of DMH 213 and the silver chloride 214.

FIG. 14 shows an alternative embodiment comprising a dispenser 216 having a first housing 217 containing a compartment 218 and a second housing 219 with a compartment 220 therein. Located in compartment 218 is a silver ion donor such as silver chloride 221 and located in compartment 220 is a source of DMH 222. A set of openings 223 allows water access to compartment 218 and to the silver chloride 221. Similarly, a set of openings 224 allows water access to compartment 220 and the source of DMH 222. It is noted that although FIGS. 13 and 14 shows the use of the silver ion donor as comprising silver chloride, other types of silver ion donors and other alternative bactericides whose solubility can be changed in the presence of DMH can also be used such as silver bromide.

In regards to the source of DMH 213, 222 of FIGS. 13 and 14, note that FIG. 13 shows a source of DMH 222 in particle form with the aforementioned particles having an initial size that is larger than the size of opening 223 to prevent the DMH particles from escaping through opening 223. FIG. 13 shows a source of DMH 213 in tablet form. In regards to the DMH tablets, it is noted that various types of material, including but not limited to microcrystalline cellulose (MCC), may be used as a binder in the formation of the DMH tablets which are tabletized with the metal ion donor so that both the DMH and the metal ion donor can be placed in the body of fluid to be treated.

It is also noted that a preferred level of the DMH present in the body of water is between 5 ppm and 25 ppm with the DMH and the source of silver cooperating to maintain a level of silver ions present in the amount of 1 to 3 ppb and/or alternatively cooperating to maintain a level of silver ions present to sustain a standard plate count at 35 degrees F. of less than 200 colonies per milliliter. The level of the compound containing a hydantoin ring can be maintained at relatively low levels and may depend on the hydantoin selected. In some cases a minimum of 5 ppm is sufficient and in other cases may be less depending on the compound containing the hydantoin ring, however, the amount of the compound containing the hydantoin ring may be established by trial and error, particularly if the compound containing the hydantoin ring contains any biocidal properties. In general a level of 5 ppm of the compound containing a hydantoin ring is sufficient if the compound containing the hydantoin ring lacks any biocidal properties.

The invention can include the step of placing the dispenser 210, 216 containing both the source of DMH 213, 222 and the silver chloride 214, 221 in the body of water and allowing water to come into contact with the source of DMH 213, 222 and the silver chloride 214, 221 to periodically release DMH and silver ions into the body of water. As the DMH is released into the body of water, the DMH is carried to the silver chloride 14, 221 and interacts with the silver chloride 214, 221 to increase the solubility of the silver ions to allow for the release of more silver ions into the body of water than the silver chloride 214, 221 alone.

The invention can also include a method of treating a body of water to kill microorganisms by maintaining an effective concentration biocides comprising the steps of: (a) adding a silver salt 214, 221 to the body of water; and (2) adding a concentration 5,5-dimethylhydantoin (DMH) 213, 222 to the body of water to interact with the silver salt 214, 221 to maintain a silver ion concentration effective to kill microorganisms. The aforementioned method can also include the steps of (3) adding silver chloride 214, 221 to the body of water; (4) adding silver bromide to the body of water (5) treating a body of recreational water for at least partial human immersion therein; (6) placing a dispenser 210, 216 containing both the silver salt 214, 221 and the 5,5-dimethylhydantoin 213, 222 in the body of water and allowing water to come into contact with both the silver salt 214, 21 and the 5,5-dimethylhydantoin 213, 222; and (7) adding silver chloride to the body of water on a carrier of limestone.

For example, in a pool system having a pool containing a body of water a halogen generator such as a chlorine generator may be used to maintain a chlorine concentration of between 0.25 ppm to 1 ppm in the body of water while a dispenser containing a source of silver ions and a compound containing a hydantoin ring can be used therewith to maintain the pool in a sanitized condition. Similarly, in a spa system containing a body of water a bromine generator may be used to maintain a lesser bromine concentration in the body of water. While a dispenser containing a halogen and a source of silver ions, a compound containing a hydantoin ring can maintain the pool in a sanitized condition. Thus in systems where halogens are used as part of the sanitizers the level of halogen present in the body of water can be reduced to thereby reduce adverse effects of halogens.

The systems described herein provide low cost easy to use systems that are consumer friendly and can be used in an in home spa or swimming pool or the like.

In summary, as FIG. 9 shows, that compounds containing a hydantoin ring, which may not have antibacterial properties such as 5,5-dimethylhydantoin (DMH), can interact with metal ion donors including silver metal ion donors such as silver bromide to increase the solubility of the silver bromide in a supply of water and aid in the sanitation process. For example, it has been found that with a silver ion donor in the presence of DMH in a liquid such as water, the dissolved silver concentrations are higher than anticipated when compared to a control solution without the presence of DMH even though the DMH lacks antimicrobial properties. In addition, the dissolved silver concentration also increases with time. The results suggested that compounds containing a hydantoin ring interact with silver to form a soluble complex even if the source(s) of silver are from insoluble salts such as silver bromide, which in some cases may be derived from silver chloride. It has also been found that compounds that contain a hydantoin ring which do have antimicrobial properties such as halogenated hydantoins including for example, Bromochlorodimethylhydantoin (BCDMH) and Dichlorodimethylhydatoin (DCDMH) also provide for greater availability of metal ions.

In the example described herein the effectiveness of the sanitizing metal ions, particularly the silver ions, is enhanced through increasing the solubility of the silver ions by addition of a compound or compounds containing a hydantoin ring in the presence of water regardless of whether the compound containing a hydantoin ring contains a halogen.

While the body of water which are particularly well suited for the invention are recreation bodies of water other bodies of water such as used for therapeutic or other human external contact may be used with the inventions described herein.

The invention described herein includes a system for maintaining a body of water in a sanitized condition by use of either a source of metal ions and a halogen generator generating a minimum halogen level sufficient to maintain the body of water in a sanitized condition or by decreasing the minimum halogen level by as much as 50% to 75% while adding a compound containing a hydantoin ring to the body of water. By sufficient to maintain the body of water in a sanitized condition is understood to mean to render the body of water free of harmful microorganisms as evidenced by tests described herein.

Thus the invention includes a method of maintaining a body of water for external human contact in a sanitized condition with use of a halogen and a source of silver ions as the sole sanitizers wherein the halogen is maintained at less than 0.5 ppm if the halogen is chlorine by adding a compound containing a hydantoin ring to the body of water. Similarly the level of bromine can be reduced if used with the compound containing a hydantoin ring and a source of silver ions.

More specifically, the method includes maintaining a body of water for external human contact in a sanitized condition with use of a halogen generator and a source of silver ions as sanitizers by setting the halogen generator to generate between 0.25 and 0.5 ppm in the body of water if the halogen is chlorine and setting the halogen generator to generate less than 2 ppm in the body of water if the halogen is by bromine and adding at least 5 ppm of a compound containing a hydantoin ring to the body of water.

The invention also includes the method of maintaining a recreational body of water and a level of halogen in the body of recreational water with a halogen generator and the sanitized condition of the body of water is characterized by any or all of the following conditions: (a) an organism count in a recreational body of water of less than 200 bacteria per milliliter; (b) a number of coliform bacteria in the recreational body of water less than 2 organisms per 100 milliliter; or (c) a number of entercoccal organisms in the recreational body of water less than 4 organisms per 100 milliliter.

The invention further includes the maintaining of a body of water in the sanitized condition wherein a halogen and a source of silver ions, which would normally require at least 0.5 ppm of chlorine in conjunction with the source of silver ions, by maintaining the chlorine level at 0.25 ppm to 0.5 ppm and adding a compound contain the hydantoin ring, which may lack sanitizing properties to the body of water.

The invention claimed is:

1. A method of maintaining: (a) an organism count in a body of water of less than 200 bacteria per milliliter; (b) a number of coliform bacteria in the recreational body of water less than 2 organisms per 100 milliliter; and (c) a number of entercoccal organisms in the recreational body of water less than 4 organisms per 100 milliliter with the use of a chlorine generator to maintain chlorine level of less than 0.5 ppm by adding a source of silver ions with a compound containing a hydantoin ring to the body of water.

2. The method of claim 1 wherein the compound containing a hydantoin ring is DMH and the source of silver ions comprises silver chloride.

3. The method of claim 1 wherein the compound containing a hydantoin ring is an unhalogenated compound and the only sanitizers used to sanitize the body of water are the chlorine and the source of silver ions.

4. The method of claim 1 wherein the chorine concentration in the water is maintained between 0.25 ppm and 0.5 ppm and the compound containing a hydantoin ring is maintained at least 5 ppm.

5. The method of claim 1 wherein the chlorine level in the body of water is maintained solely with the chlorine generator.

6. A method of maintaining a body of water for external human contact in a sanitized condition with use of a chlorine generator and a source of silver ions as sanitizers by setting the chlorine generator to generate between 0.25 and 0.5 ppm chlorine in the body of water and adding at least 5 ppm of a compound containing a hydantoin ring to the body of water.

7. The method of claim 6 wherein the body of water is a recreational body of water and amount of chlorine is maintained with the generator and the sanitized condition of the body of water is characterized by any or all of the following conditions: (a) an organism count in a recreational body of water of less than 200 bacteria per milliliter; (b) a number of coliform bacteria in the recreational body of water less than 2 organisms per 100 milliliter; or (c) a number of entercoccal organisms in the recreational body of water less than 4 organisms per 100 milliliter and the halogen and the source of silver ions are the sole sanitizers in the body of water.

* * * * *